US012721948B2

(12) United States Patent
Yang

(10) Patent No.: US 12,721,948 B2
(45) Date of Patent: Sep. 1, 2026

(54) UNILATERALLY DRIVEN DRUG INFUSION SYSTEM

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 622 days.

(21) Appl. No.: 18/035,525

(22) PCT Filed: Aug. 23, 2021

(86) PCT No.: PCT/CN2021/114035
§ 371 (c)(1),
(2) Date: May 5, 2023

(87) PCT Pub. No.: WO2022/116601
PCT Pub. Date: Jun. 9, 2022

(65) Prior Publication Data

US 2023/0330330 A1 Oct. 19, 2023

(30) Foreign Application Priority Data

Dec. 4, 2020 (WO) ................ PCT/CN2020/133734

(51) Int. Cl.
*A61M 5/172* (2006.01)
*A61B 5/00* (2006.01)
(Continued)

(52) U.S. Cl.
CPC ....... *A61M 5/1723* (2013.01); *A61B 5/14503* (2013.01); *A61B 5/14532* (2013.01);
(Continued)

(58) Field of Classification Search
CPC ............ A61B 2560/045; A61B 5/0004; A61B 5/1118; A61B 5/1126; A61B 5/721;
(Continued)

(56) References Cited

U.S. PATENT DOCUMENTS

2005/0215947 A1* 9/2005 Heruth .............. A61M 5/14276 604/66
2009/0105650 A1 4/2009 Wiegel et al.
(Continued)

FOREIGN PATENT DOCUMENTS

CN 103007381 4/2013
CN 109313524 2/2019
(Continued)

OTHER PUBLICATIONS

"International Search Report (Form PCT/ISA/210) of PCT/CN2021/114035," mailed on Nov. 23, 2021, pp. 1-2.

*Primary Examiner* — Lauren P Farrar
(74) *Attorney, Agent, or Firm* — JCIP GLOBAL INC.

(57) ABSTRACT

A unilaterally driven drug infusion system, includes: an infusion unit, including a reservoir, a piston and a screw, the piston arranged in the reservoir; a driving unit including a rotating shaft and a driving member, the driving member including a driving end; a driving wheel provided with wheel teeth; a linear actuator and a reset unit respectively connected to the driving member; a control unit controlling the linear actuator or the reset unit to apply different driving powers on the driving member; and a sensing unit operatively connected to the control unit and used to sense or recognize the user's body movements, and different body movements represent different functional instructions, and according to the body movements sensed or recognized by the sensing unit. The control unit controls the infusion unit to execute corresponding functional instructions.

15 Claims, 9 Drawing Sheets

(51) Int. Cl.

| | |
|---|---|
| ***A61B 5/145*** | (2006.01) |
| ***A61M 5/14*** | (2006.01) |
| ***A61M 5/142*** | (2006.01) |
| ***A61M 5/145*** | (2006.01) |
| ***A61M 5/168*** | (2006.01) |
| ***G16H 20/17*** | (2018.01) |

(52) U.S. Cl.
CPC ............ *A61B 5/746* (2013.01); *A61B 5/7475* (2013.01); *A61M 5/14* (2013.01); *A61M 5/142* (2013.01); *A61M 5/14248* (2013.01); *A61M 5/1452* (2013.01); *A61M 5/16804* (2013.01); *A61M 5/16831* (2013.01); *G16H 20/17* (2018.01); *A61B 2562/0219* (2013.01); *A61M 2005/14208* (2013.01); *A61M 2205/103* (2013.01); *A61M 2205/276* (2013.01); *A61M 2205/33* (2013.01); *A61M 2209/01* (2013.01); *A61M 2230/201* (2013.01)

(58) Field of Classification Search
CPC . A61B 5/14503; A61B 5/14532; A61B 5/746; A61B 5/7475; A61B 2562/0219; A61B 2560/0443; A61M 2005/1726; A61M 2230/005; A61M 2230/62; A61M 2205/3584; A61M 2230/63; A61M 2205/18; A61M 2205/3334; A61M 5/1723; A61M 5/14; A61M 5/142; A61M 5/14248; A61M 5/1452; A61M 5/16804; A61M 5/16831; A61M 2005/14208; A61M 2205/103; A61M 2205/276; A61M 2205/33; A61M 2209/01; A61M 2230/201; H04L 2209/88; H04L 9/3231; G16H 20/17
See application file for complete search history.

(56) References Cited

U.S. PATENT DOCUMENTS

| | | | |
|---|---|---|---|
| 2013/0178744 | A1 | 7/2013 | Kierulf et al. |
| 2014/0128739 | A1 | 5/2014 | Sundaran et al. |

FOREIGN PATENT DOCUMENTS

| | | | | |
|---|---|---|---|---|
| CN | 111939371 | | 11/2020 | |
| WO | WO-2009026060 | A2 * | 2/2009 | ........ A61M 5/14216 |

* cited by examiner

UNILATERALLY DRIVEN DRUG INFUSION SYSTEM

CROSS-REFERENCE TO RELATED APPLICATION

This application is a 371 of international application of PCT application serial no. PCT/CN2021/114035, filed on Aug. 23, 2021, which claims the priority benefit of PCT application no. PCT/CN2020/133734, filed on Dec. 4, 2020. The entirety of each of the above-mentioned patent applications is hereby incorporated by reference herein and made a part of this specification.

TECHNICAL FIELD

The present invention mainly relates to the field of medical instruments, in particular to a unilaterally driven drug infusion system.

BACKGROUND

A drug infusion system can continuously deliver drug into a patient's body for disease treatment. Drug infusion systems are widely used in the field of diabetes treatment, which continuously infuse required dosage of insulin into the patient's subcutaneous tissue, thereby simulating the secretion function of the pancreas to keep the blood glucose stable. The drug fluid is usually stored inside the infusion pump. The existing drug infusion system, controlled by remote device, is usually attached directly on the patient's skin through a medical adhesive tape.

Currently, when a user uses an infusion system, he needs to find different inputting positions on the remote device to manually input functional instruction, and then control the infusion pump to perform corresponding functions. This inputting process is cumbersome, which worsens the user experience infusion system.

Therefore, in the prior art, there is an urgent need for an infusion system that simplifies the functional instruction inputting process and has a better user experience.

BRIEF SUMMARY OF THE INVENTION

The embodiment of the invention discloses a unilaterally driven drug infusion system, the user's body movement, as a functional instruction, is sensed by a sensing unit, the control unit can control the infusion unit to execute the corresponding function without the user manually inputting the functional instruction on the remote device, enhancing the user experience.

The invention discloses a unilaterally driven drug infusion system, comprising: an infusion unit, includes a reservoir, a piston and a screw, the piston, connected with the screw, is arranged in the reservoir; a driving unit including at least one rotating shaft and at least one driving member, and the driving member includes at least one driving end, the driving member can rotate around the rotating shaft to advance or reset the driving end; at least one driving wheel provided with wheel teeth, and the advancing driving end can push the wheel teeth to rotate the driving wheel, thereby driving the screw forward; a linear actuator and a reset unit respectively connected to the driving member, the linear actuator and the reset unit respectively apply driving power to the driving member to advance and reset the driving end; a control unit, connected to the linear actuator or the reset unit, controls the linear actuator or the reset unit to apply different driving powers on the driving member; and a sensing unit operatively connected to the control unit and used to sense or recognize the user's body movements, and different body movements represent different functional instructions and manual inputting, and according to the body movement sensed or recognized by the sensing unit, the control unit controls the infusion unit to execute corresponding functional instructions.

According to an aspect of the present invention, the functional instructions include infusing drug or stopping infusing drug, priming the infusion needle, puncturing or retracting the infusion needle, adjusting the infusion speed or infusion mode, adjusting the amount of drug infusion, turning on or off the alarm, connecting or disconnecting the remote device, switching the user's physical state, or starting the event.

According to an aspect of the present invention, the sensing unit is provided with one or more of acceleration sensor, inclination sensor, vibration sensor and rotation sensor.

According to an aspect of the present invention, the body movements include one or a combination of jumping, squatting, leg movements, arm movements, taps on the sensing unit, bending over, torso twist, special way of walking.

According to one aspect of the present invention, the body movement sensed or recognized by the sensing unit within a fixed time period t is recognized as a valid body movement, and beyond the fixed time period t, the body movement is recognized as an invalid body movement.

According to one aspect of the present invention, the fixed time period t is 0.5 s-5 s.

According to one aspect of the present invention, the fixed time period t is 1 s.

According to an aspect of the present invention, the sensing unit is integrated in the infusion unit or control unit.

According to an aspect of the present invention, the sensing unit, the control unit and the infusion unit are arranged in one device.

According to an aspect of the present invention, the infusion unit and the control unit are designed separately, and the control mechanism module can be reused.

According to an aspect of the present invention, the infusion unit and the control unit are disposed in one housing, discarded together after a single use.

According to an aspect of the present invention, it further includes a body movement verification unit which is connected to the sensing unit.

According to an aspect of the present invention, the driving member have a variety of different operating modes, thereby making the infusion system have various different infusion increments or infusion rates.

Compared with the prior art, the technical solution of the present invention has the following advantages:

In the unilaterally driven drug infusion system disclosed in the present invention, the sensing unit operatively connected to the control unit and used to sense or recognize the user's body movements, and different body movements represent different functional instructions, and according to the body movement sensed or recognized by the sensing unit, the control unit controls the infusion unit to execute corresponding functional instructions. Compared with manual inputting, body movements are directly used as functional instructions, avoiding the user from searching the inputting position of the functional instructions on the remote device and manual inputting, which is simple and convenient, and improves the user experience as well.

Furthermore, the body movements include one or a combination of jumping, squatting, leg movements, arm movements, taps on the sensing unit, bending over, torso twist, special way of walking. There are many types of body movements which are relatively easy to be performed by users. At the same time, the combination of multiple body movements also improves the flexibility in the manufacturing process in the factory or the operating process for user. And generally, the more types of body movements included by one functional instruction, the safer of the artificial pancreas while executing them.

Furthermore, the sensing unit provided with one or more of the acceleration sensor, inclination sensor, vibration sensor and rotation sensor. A variety of motion sensors can be selected and combined to improve the accuracy and sensitivity of identifying body movements.

Further, the acceleration sensor is a three-axis acceleration sensor. The three-axis acceleration sensor can detect the change of acceleration in X, Y and Z axes, with the advantage of rapid detection of body movements, improving the sensitivity of movement detection.

Further, the body movements sensed or recognized within a fixed time period t by the sensing unit are recognized as valid movements, beyond the fixed time period t, the body movements by the sensing unit are recognized as invalid movements, which prevents the execution of false instructions from excess body movements of users, and improves the security of the system.

Furthermore, the sensing unit is integrated in the infusion unit or the control unit, or the sensing unit, control unit, sensor and infusion unit are arranged in a single device. The integrated design of multiple units in a single device can improve the integration degree of the infusion system, which facilitates the user's daily physical activities, and further enhances the user experience.

Furthermore, the infusion system further includes a body movement verification unit which is connected to the sensing unit. The movement verification unit is used to confirm whether the user's body movements meet the standard or the requirements preset in this unit, improving the safety of the infusion system infusion system.

Furthermore, the driving member have a variety of different operating modes, thereby making the infusion system have various different infusion increments or infusion rates. When the infusion system has a variety of different infusion increments or infusion rates, the user or closed-loop system can arbitrarily choose the appropriate infusion mode to accurately control the level of body fluids according to the actual requirements of the body, improving the user experience.

DETAILED DESCRIPTION

Figure 1A:
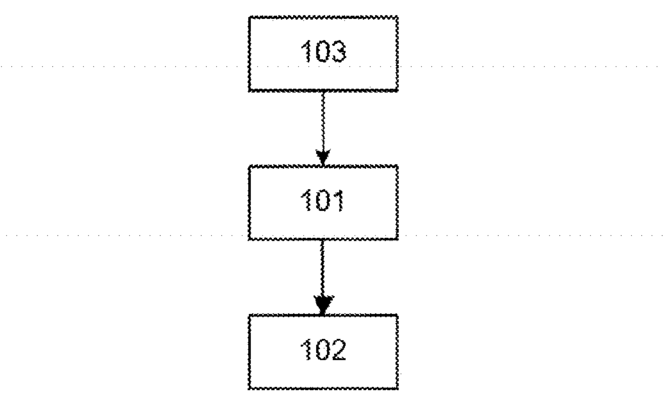
FIG. 1*a* is a schematic view of the unit structure of a unilateral driven drug infusion system according to an embodiment of the present invention.

As mentioned above, when a user uses the prior art infusion system, he needs to find different inputting positions on the remote device to manually input functional instruction, and then control the infusion pump to perform corresponding functions. This inputting process is cumbersome, which worsens the user experience.

In order to solve this problem, the present invention provides a unilaterally driven drug infusion system, the sensing unit operatively connected to the control unit and used to sense or recognize the user's body movements, and different body movements represent different functional instructions, and according to the body movement sensed or recognized by the sensing unit, the control unit controls the infusion unit to execute corresponding functional instructions. Compared with manual inputting, body movements are directly used as functional instructions, avoiding the user from searching the inputting position of the functional instructions on the remote device, which is simple and convenient, and improves the user experience as well.

Various exemplary embodiments of the present invention will now be described in detail with reference to the drawings. The relative arrangement of the members and the steps, numerical expressions and numerical values set forth in the embodiments are not to be construed as limiting the scope of the invention.

In addition, it should be understood that, for ease of description, the dimensions of the various members shown in the figures are not necessarily drawn in the actual scale relationship, for example, the thickness, width, length or distance of certain units may be exaggerated relative to other structures.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in following description of the drawings.

FIG. 1*a* is a schematic view of the unit structure of a unilateral driven drug infusion system according to an embodiment of the present invention; FIG. 1B-FIG. 1*e* are schematic top views of a unilateral driven drug infusion system, respectively, according to four different embodiments of the present invention.

The unilateral driven drug infusion system includes an adhesive patch 100, control unit 101, infusion unit 102 and sensing unit 103.

The control unit 101 is used to control the driving power output by the linear actuator or by the reset unit inside the infusion unit 102 to control the drug infusion. The control unit 101 can also establish wireless communication with a remote device, and the like.

The infusion unit 102 includes various units for realizing the function for drug infusion, which will be described in detail below.

The sensing unit 103 is used to sense and recognize body movements from the user, provided with one or more of the acceleration sensor, inclination sensor, vibration sensor and rotation sensor.

In the embodiment of the invention, the sensing unit 103 is only provided with a three-axis acceleration sensor, which can detect the change of acceleration in X, Y and Z axis directions, and has the advantage of rapid detection of body movements, more comprehensive recognition of body movements, and improved sensitivity of movement detection.

In another embodiment of the invention, the sensing unit 103 is only provided with rotation sensor, which can accurately detect the user's rotation and other body movements, such as turning in a circle, etc.

In another embodiment of the invention, the sensing unit 103 is only provided with a vibration sensor, and the vibration sensor can accurately detect the user's flapping and other body movements.

In another embodiment of the invention, the sensing unit 103 is provided with a combination of a three-axis acceleration sensor, a rotation sensor and a vibration sensor. The combined motion sensor can realize more and more accurate detection of body movements, enrich the choice of the user and improve the user experience.

The control unit 101 and the sensing unit 103 are operatively connected to facilitate the transmission of instruction signals between the two units. Here, the term "operatively connected" means that the control unit 101 can directly or indirectly obtain body movement information from the sensing unit 103, thereby controlling the infusion unit 102 to perform the corresponding functional instructions, which will be described below in conjunction with different embodiments.

In the embodiment of the present invention, the sensing unit 103 are connected to control unit 101. Herein, the term "connected" means that the control unit 101 and the infusion unit 102 are electrically or wirelessly connected to each other. And the "connected" of any two units or any two structures hereinafter has the same meaning.

Preferably, in the embodiment of the present invention, the sensing unit 103 and the control unit 101 are electrically connected. The electrical connection between the two not only facilitates structural design, but also reduces power consumption compared with the wireless connection. Therefore, the control unit 101 can control the infusion unit 102 to execute corresponding functional instructions, as shown in FIG. 1*a*.

Obviously, in the embodiment of the present invention, the functional instructions include the functions that the infusion unit 102 can perform, such as including but not limited to infusing drug or stopping infusing drug, priming the infusion needle, puncturing or retracting the infusion needle, adjusting the infusion speed or infusion mode, adjusting the amount of drug infusion, starting the event, switching the user's physical state, and connecting or disconnecting the remote device.

In the embodiment of the present invention, the infusion of drugs includes basal dose infusion and bolus dose infusion. Adjusting the infusion speed or the infusion mode means that according to the user's physical state, the user reasonably selects or the artificial pancreas auto-selects the driving type or the driving mode of the driving unit in the infusion unit 102, thereby achieving the goal of optimal blood glucose (BG) controlling. Connecting or disconnecting the remote device means that the user can choose whether to connect the infusion unit 102 to the remote device according to actual needs. Switching the user's physical state means that the user switches from the sitting state to the sleeping state, or from the sleeping state to the wake-up state, etc. Starting the event means indicating the user's meal event, sports event, or bathing event.

The functions performed by the unilaterally driven drug infusion system in the embodiment of the present invention are controlled by the user's body movements. Therefore, in the embodiment of the present invention, different body movements of the user represent different functional instructions. In the embodiment of the present invention, the body movement includes one or a combination of jumping, squatting, leg movements, arm movements, taps on the sensing unit, bending over, torso twist, special way of walking. Compared with manual inputting, body movements are much easier to implement, which improves the user experience.

It should be noted here that tapping the sensing unit 103 not only includes direct contact with the sensing unit 103, but also includes indirect contact or non-contact. For example, the user can tap the clothing around the sensing unit 103. Leg movements include, but are not limited to, raising the leg and shaking the leg. Arm movements include, but are not limited to, vibrating arms and swinging arms. Special walking methods include, but are not limited to, forward and backward walking, circle walking and zigzag.

In the embodiment of the present invention, the functional instructions are represented by single movement or a combination of multiple movements among the above-mentioned body movements, and no limit is set on the frequency of a certain body movement. Preferably, in the embodiment of the present invention, the functional instruction for priming the infusion needle is to tap the sensing unit 103 three times. Tapping three times is chosen instead of one, two, or more than three times, which avoids the interference caused by accidental movements, and is more convenient and more user-friendly than tapping more than three times. In another embodiment of the present invention, the functional instruction for the basal dose infusion is that the user bends down first, and then twists the torso twice. In still another embodiment of the present invention, the functional instruction for connecting or disconnecting the remote device (such as a Personal Diabetes Manager (PDM), mobile phone, ipad, etc.) is zigzagging.

In order to avoid the interference caused by unnecessary or wrong body movements, users need to complete the body movements corresponding to the expected instructions within a fixed time period t. Here, the fixed time period t can be set to any time within 0.5 s-5 s according to the habits of users. Preferably, t=1 s. For example, in the embodiment of the present invention, the user taps the sensing unit 103 three times within 1 s, which is a valid body movement to perform the function instruction of calibrating the infusion unit 102, but because of external factors, the user taps the sensing unit 103 one more time after 1 s, this is an invalid body movement. If there is no fixed time period t to limit, the body movement combination may be recognized as other functional instructions.

It should be noted that the body movements or the combination of body movements corresponding to the above functional instructions are not unique. Users can set the corresponding body movements or the combination of body movements according to their own habits and condition.

Figure 1B:
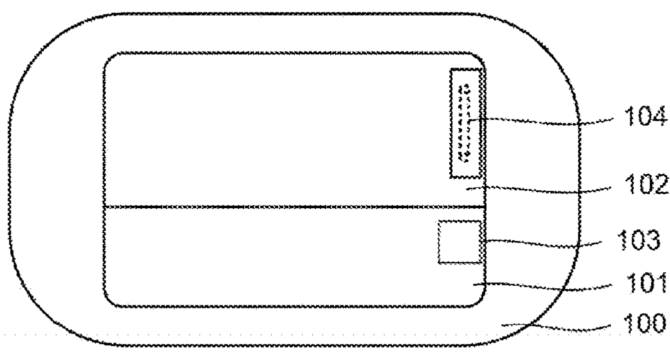
FIG. 1B-FIG. 1*e* are schematic top views of a unilateral driven drug infusion system, respectively, according to four different embodiments of the present invention.
Figure 1C:
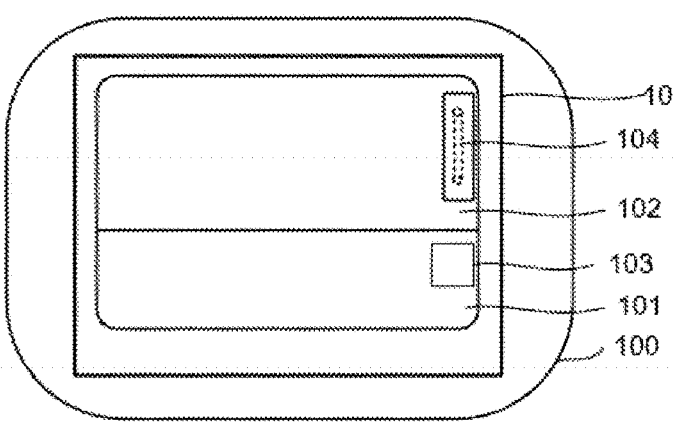
Figure 1D:
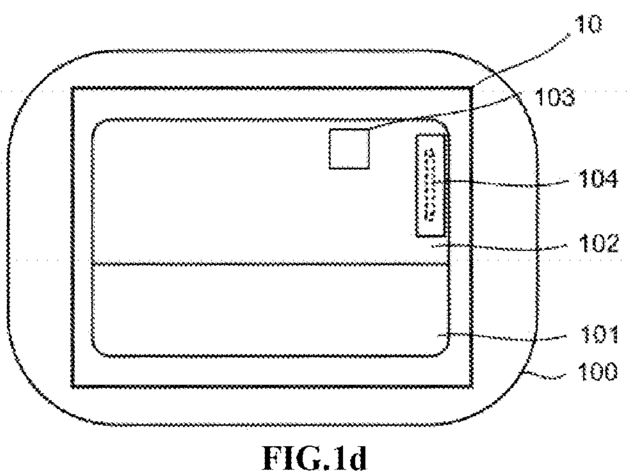

In the embodiment of the present invention, the infusion unit 101 and the control unit 102 are designed separately and connected by a waterproof plug or directly engaged and electrically connected into a whole. the infusion unit 101 can be reused, the infusion unit 102 is discarded after a single use. The sensor unit 103 is integrated in the control unit 101 or the infusion unit 102, and attached to a certain position of the user's skin by the adhesive patch 100. Preferably, the sensor unit 103 is integrated in the control unit 100, which can be reused with the control unit 101 to reduce user's use cost, as shown in FIG. 1B. In another embodiment of the present invention, the sensor unit 103 is directly integrated in the control unit 101 or the infusion unit 102, but the control unit 100 and the infusion unit 101 are disposed in one device 10 and connected with a wire, attached to a certain position of the user's skin by the adhesive patch 100, and discarded together after a single use, as shown in FIG. 1*c* and FIG. 1*d*.

Figure 1E:
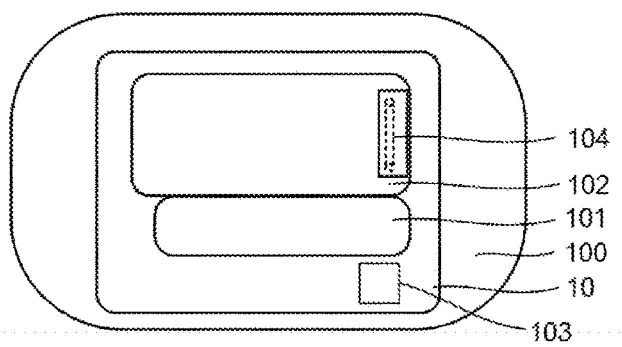

In the other embodiment of the present invention, the sensor unit 103 isn't integrated in the control unit 101 or the infusion unit 102 directly, but the sensing unit 103, the control unit 101 and the infusion unit 102 are arranged in one device 10, the infusion unit 101 and the control unit 102 can be designed separately or together, that is connected with a wire, and discarded together after a single use, as shown in FIG. 1*e*.

The integrated design of multiple units in a single device can improve the integration degree of the infusion system, which facilitates the user's daily physical activities, and further enhances the user experience.

Figure 2A:
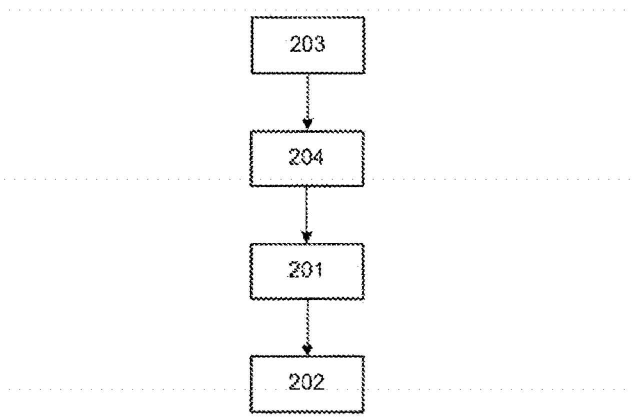
FIG. 2*a*-FIG. 2*b* are schematic views of the unit structure of a unilateral driven drug infusion system including a movement verification unit according to two different embodiments of the present invention.
Figure 2B:
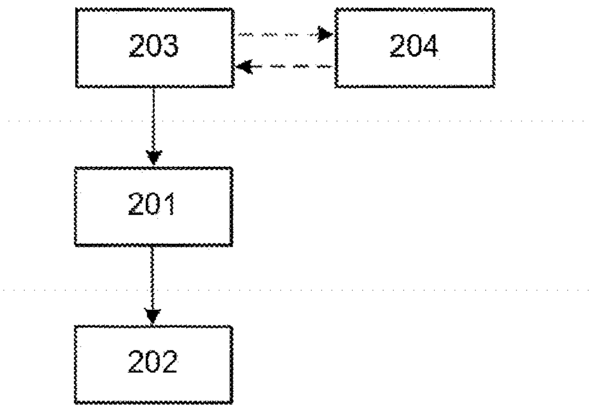

FIG. 2*a*-FIG. 2*b* are schematic views of the unit structure of a unilateral driven drug infusion system including a movement verification unit according to two different embodiments of the present invention.

The movement verification unit 204 is connected with the sensing unit 203 and is used to confirm whether the user's body movements meet the standard or the requirements (such as speed, intensity, or frequency preset), so as to improve the safety of drug infusion system. When the sensing unit 203 detects a user's specific body movement which does not meet the preset requirements or the standard, the drug infusion system will issue a specific form of alarm (such as light, sound, vibration, etc.), allowing the user to perform more standard body movement again. Similarly, when the body movement meets the requirements or the standard, the artificial pancreas can also send out a specific form of warning (such as light, sound, vibration, etc.).

The embodiment of the present invention does not specifically limit the position of the movement verification unit 204 and its connection relationship with other units, as long as the condition for the movement verification unit 204 to be connected to the sensing unit 203 can be met. Preferably, in the embodiment of the present invention, the movement verification unit 204 is provided between the sensing unit 203 and the control unit 201, as shown in FIG. 2*a*. Therefore, after the sensing unit 203 senses or recognizes the user's body movement, the movement verification unit 204 confirms whether the movement meets the requirements or the standard. If met, the control unit 201 receives the body movement information indirectly from the sensing unit 203, thereby controlling the infusion unit 202 to execute the corresponding functional instruction. At this time, sensing unit 203 is operatively connected with the control unit 201.

In another embodiment of the present invention, the movement verification unit 204 may also only be connected to the sensing unit 203, as shown in FIG. 2*b*. When the movement verification unit 204 confirms that the body movement meets the requirements or the standard, the control unit 201 can obtain the corresponding instruction information directly, and then control the infusion unit 202 to execute the corresponding functional instruction.

As mentioned above, here, "connected" refers to that the movement verification unit 204 and the sensing unit 203 are electrically or wirelessly connected to each other.

The unilaterally driven drug infusion system further comprises an infusion needle 104. One end of the infusion needle 104 is connected to the outlet of the reservoir, while the other end pierces the skin to infuse the drug subcutaneously. In the embodiment of the present invention, the infusion needle 104 is disposed at one end of the infusion unit 102. In other embodiments of the present invention, the infusion needle 104 may be disposed at other positions according to its functions or structural features of the device, such as being disposed at the middle portion of the device, which is not specifically limited herein. The infusion needle 104 is a rigid infusion needle or a flexible infusion needle, or designed according to its different positions and functions, the design of infusion needle 104 can also adopt a combination of rigid infusion needle(s) and flexible infusion needle(s), which is not specifically limited herein. Preferably, in the embodiment of the present invention, the infusion needle 104 is a rigid infusion needle.

Figure 3:
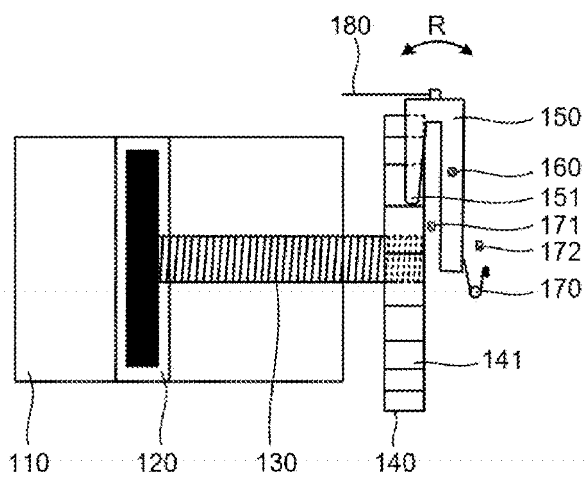
FIG. 3 is a schematic diagram of main structures in the infusion unit according to an embodiment of the present invention.

FIG. 3 is a schematic diagram of main structures in the infusion unit 102 according to an embodiment of the present invention.

The internal structure of the infusion unit 102 mainly includes at least a reservoir 110, a piston 120, a screw 130, a driving wheel 140, a driving unit (not shown), a reset unit 170 and a linear actuator 180. The driving unit includes at least one driving member 150 and at least one rotating shaft 160. In the embodiment of this present invention, the driving member 150 is connected to the reset unit 170 and the linear actuator 180, respectively. It should be noted that the connection herein includes mechanical connection or electrical connection.

The reservoir 110 is used for storing liquid drug. Drugs include, but are not limited to, insulin, glucagon, antibiotics, nutrient solutions, analgesics, morphine, anticoagulants, gene therapy drugs, cardiovascular drugs or chemotherapy drugs, etc.

The piston 120 is used to infuse liquid drug into the body.

The screw 130 is connected to the piston 120 and the driving wheel 140, respectively. In the embodiment of the present invention, the driving wheel 140 advances the screw 130 forward by screwing, the screw 130 then forces the piston 120, arranged in the reservoir 110, to move forward, so as to achieve the purpose of drug infusion. When the screw 130 is a flexible screw, the screw 130 may be designed to be curved. In one embodiment of the invention, the flexible screw is formed by a plurality of threaded sub-units movably connected one by one.

The peripheral surface of the driving wheel 140 is provided with wheel teeth 141. The wheel teeth 141 are gear teeth or ratchet teeth. Specifically, in the embodiment of the present invention, for improving driving efficiency, the wheel teeth 141 are ratchet teeth which can be pushed more easily.

One driving end 151 is provided on the driving member 150 to push the wheel teeth 141, thereby rotating the driving wheel 140. The driving member 150 is movably connected to the rotating shaft 160.

The linear actuator 180 and the reset unit 170 cooperate with each other to make the driving member 150 rotate reciprocally around the rotating shaft 160, as shown in the R direction in FIG. 3, thereby making the driving end 151 move in the advancing direction and reset direction. When the driving member 150 performs one reciprocating rotation, the driving wheel 140 drives the screw 130 forward one step, and the screw 130 engages the piston 120 to infuse one unit of drug.

It should be noted here that the advancing direction of the driving end 151 refers to the direction in which the wheel teeth 141 moves, while the reset direction of the driving end 151 is opposite to the advancing direction. During reset, the driving end 151 only slides on the surface of the wheel teeth 141 without pushing.

In some embodiments of the present invention, the reset unit 170 at least includes a spring, an elastic piece, an elastic plate, an elastic rod, rubber and other elastic members. It should be noted that the spring herein includes a compression spring, an extension spring, or a torsion spring, etc, so as to the meaning of the spring below. Specifically, in the embodiment of the present invention, the reset unit 170 is a torsion spring which is more conducive to the reset of the driving member 150. In some embodiments of the present invention, the reset unit 170 may also be an elastic conductive member, such as a metal spring, conductive rubber, or the like. In other embodiments of the present invention, the reset unit 170 includes an electrically driven linear actuator or an electrically heated linear actuator, such as a shape memory alloy. The type, material selection or the position of the reset unit 170 are not specifically limited herein, as long as it can satisfy the condition of making the driving member 150 rotate in the reset direction.

After being energized, the physical form of the material of the linear actuator, like shape memory alloy, changes, which makes shrinkage deformation of the shape memory alloy occur, thereby outputting the driving power. The higher the current is, the larger the shrinkage deformation of the shape memory alloy occurs, and the greater the driving power outputs. Obviously, when the current is constant, the amplitude of the driving power output by the shape memory alloy is also constant, therefore the shape memory alloy can output stable and controllable driving power for drug infusion.

The linear actuator 180 is an electrically driven linear actuator or an electrically heated linear actuator. By alternately turning on and off, the linear actuator 180 outputs power in pulses. Specifically, in the embodiment of the present invention, the linear actuator 180 is a shape memory alloy.

Figure 4A:
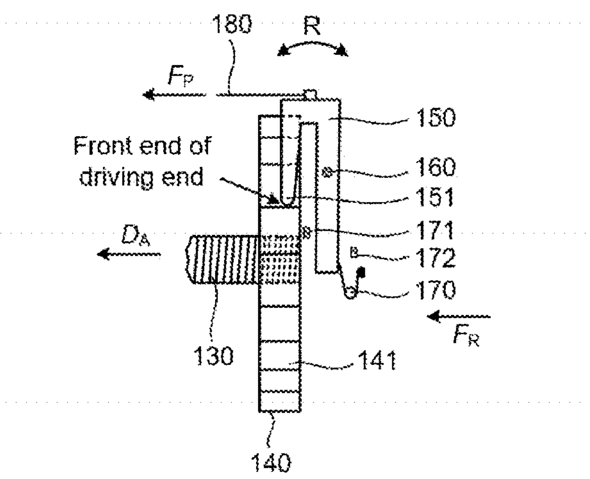
FIG. 4*a*-FIG. 4*c* are top views of the driving end pushing the wheel teeth according to different embodiments of the present invention.
Figure 4B:
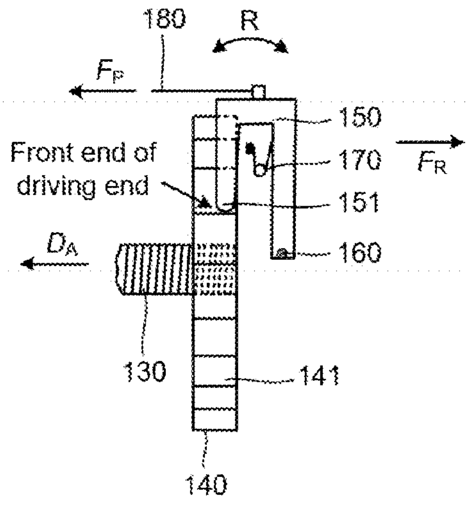
Figure 4C:
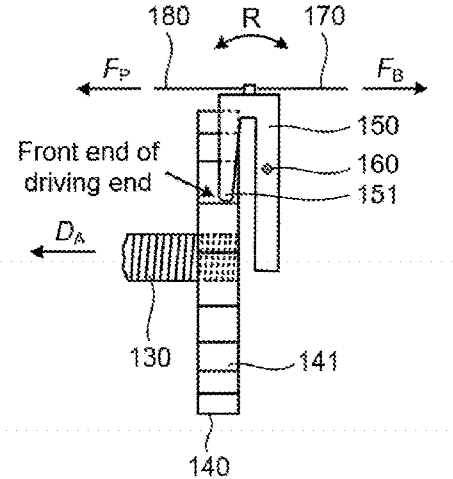
Figure 5A:
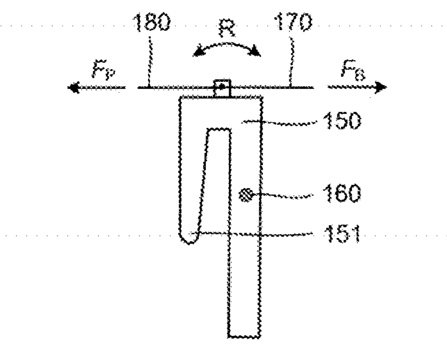
FIG. 5*a*-FIG. 5*c* are schematic diagrams of the linear actuator, the reset unit and the driving member cooperating with each other according to different embodiments of the present invention.
Figure 5B:
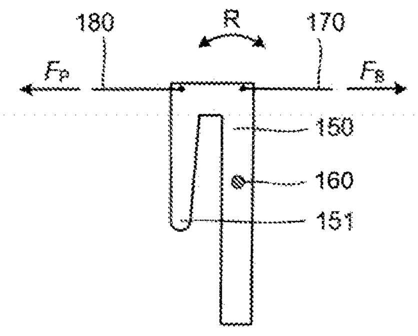
Figure 5C:
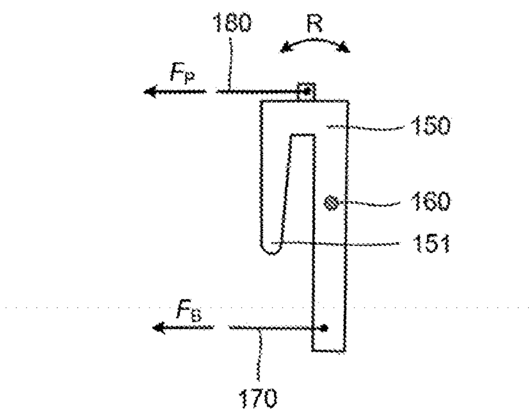

FIG. 4*a*-FIG. 4*c* are top views of the driving end 151 pushing the wheel teeth 141 in different embodiments of the present invention. FIG. 5*a*-FIG. 5*c* are schematic diagrams of the linear actuator 180, the reset unit 170 and the driving member 150 cooperating with each other in different embodiments of the present invention.

As shown in FIG. 4*a* and FIG. 4*b*, the principle of the reciprocating rotation of the driving member 150 in the embodiment of the present invention is as follows. When the linear actuator 180 pulls the driving member 150 by force $F_P$, the driving member 150 rotates counter-clockwise (advancing direction) around the rotating shaft 160, driving the driving end 151 to push the wheel teeth 141 forward, and thereby making the driving wheel 140 rotate. The driving wheel 140 then moves the screw 130 forward in $D_A$ direction. The reset unit 170, an elastic member, builds a gradually increasing elastic force $F_R$. When the linear actuator 180 stops applying force and under the action of only the elastic force $F_R$, the driving member 150 will rotate clockwise (reset direction) around the rotating shaft 160. At this time, the driving end 151 just slides on the surface of the wheel teeth 141 instead of pushing them, therefore the driving wheel 140 stops rotating. The driving member 150 completes one reciprocating rotation.

As shown in FIG. 4*b*, in another embodiment of the present invention, the reset unit 170 and the linear actuator 180 are disposed on the same side of the rotating shaft 160. And according to the general technical principles, those skilled in the art can arbitrarily adjust the positional relationship and the connection relationship of the reset unit 170, the driving member 150, and the linear actuator 180, which is not specifically limited herein, as long as the above-mentioned rotation processes can be achieved.

As shown in FIG. 4*c*, in yet another embodiment of the present invention, the reset unit 170 includes an electrically driven linear actuator or an electrically heated linear actuator, such as a shape memory alloy. Although the technical principle that the driving end 151 pushes the wheel teeth 141 is consistent with the foregoing, the driving member 150 cannot automatically reset after the driving end 151 stops advancing, therefore, the reset unit 170 is required to provide the reset force $F_B$ whose direction is opposite with that of $F_P$, thereby making the driving member 150 rotate reciprocally with the cooperation of the reset unit 170 and the linear actuator 180. Obviously, those skilled in the art can arbitrarily adjust the directions of the $F_P$ and $F_B$ as needed, as long as the conditions for reciprocating rotation of the driving member 150 are satisfied, as shown in FIG. 5*a*-FIG. 5*c*.

Preferably, as shown in FIG. 4*a* to FIG. 4*c*, in the embodiment of the present invention, the directions of $F_P$, $F_R$ (or $F_B$) and $D_A$ are parallel to one another. This parallel design can make full use of space and optimize the structural relationships inside the infusion system, making internal structure more compact.

In other embodiments of the present invention, the $F_P$ direction, the $F_R$ (or $F_B$) direction, or the $D_A$ direction may not be parallel, which is not specifically limited herein, as long as the purpose of making the driving member 150 rotate reciprocally can be achieved.

Figure 6A:
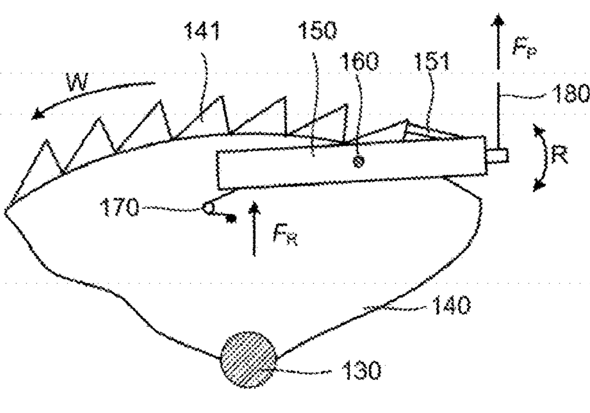
FIG. 6*a*-FIG. 6*b* are schematic diagrams of that the pulling direction of the linear actuator is not parallel to the advancing direction of the screw according to another embodiment of the present invention.
Figure 6B:
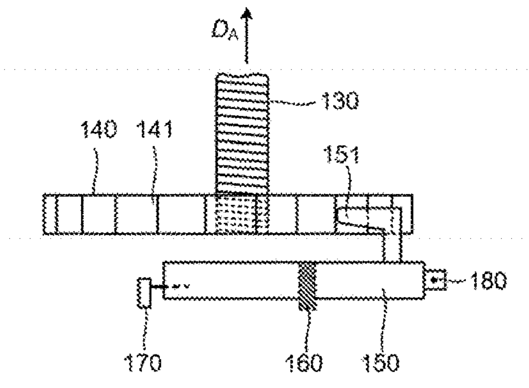

FIG. 6*a*-FIG. 6*b* are schematic diagrams of that the pulling direction of the linear actuator 180 is not parallel to the advancing direction of the screw 130. FIG. 6*b* is a top view of FIG. 6*a*.

The $F_P$ direction of the linear actuator 180 is perpendicular to the forward direction $D_A$ of the screw 130. The rotating shaft 160 and the reset unit 170 are disposed on the base 190. As described above, the driving member 150, rotating reciprocally in the R direction, drives the driving end 151 to push the wheel teeth 141, making the driving wheel 140 rotate in the W direction and driving the screw 130 to advance in the $D_A$ direction. The driving principle of the driving member 150 is consistent with the foregoing embodiment.

In the embodiment of the present invention, blocking walls 171 and 172 (as shown in FIG. 3 and FIG. 4*a*) that can stop the driving member 150 from rotating are also provided in the infusion system. And an electrical signal may be triggered when the driving member 150 contacts the blocking wall 171 or 172, allowing the control unit 101 to control the driving power output of the linear actuator 180. In another embodiment of the present invention, only the blocking wall 171 or only the blocking wall 172 may be provided, so that the rotating terminal in either direction of the driving member 150 is controlled by the control unit 101. The position of the blocking wall 171 or 172 is not specifically limited in the embodiment of the present invention, as long as the condition that the driving member 150 stops rotating can be satisfied.

In another embodiment of the present invention, no blocking wall is provided (as shown in FIG. 4*b* to FIG. 6*b*), and the rotating terminal of the driving member 150 is completely controlled by the control unit 101.

Figure 7:
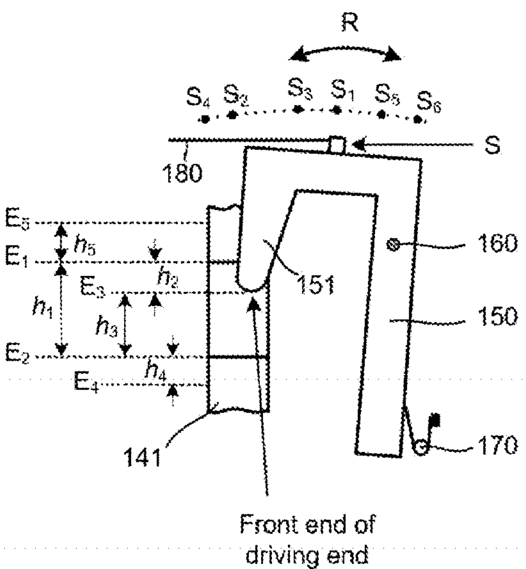
FIG. 7 is a schematic diagram of the reciprocating rotation amplitude of the driving member according to an embodiment of the present invention.

FIG. 7 is a schematic diagram of the reciprocating rotation amplitude of the driving member 150 according to an embodiment of the present invention.

The principle of the driving member 150 implementing two reciprocating rotation amplitudes according to the embodiment of the present invention is as follows. The control unit controls the magnitude of the force output of the linear actuator 180, and the reset member 170 implements resetting function, which makes the driving member 150 to reciprocate, making the driving end 151 advance or reset. $E_n$ represents the position reached by the front end of the driving end, such as $E_1$, $E_2$, $E_3$, $E_4$, and $E_5$. $h_n$ represents the distance between two different positions $E_n$. $S_n$ represents the different positions of the point S of the force output by the linear actuator 180 during the reciprocating rotation, and the dotted arc in FIG. 5 represents the trajectory of S, therefore, $S_1$, $S_2$, $S_3$, $S_4$, $S_5$ correspond with $E_1$, $E_2$, $E_3$, $E_4$, $E_5$, respectively. Obviously, the movement distance between different $S_n$ can be used to represent the rotation amplitude of the driving member 150. Specifically, in the embodiment of the present invention, $h_1$ is the pitch of wheel teeth, and $h_1=3\ h_2$. When the linear actuator 180, according to the instruction, makes the driving end 151 to advance the wheel teeth 141 from the $E_1$ to the $E_2$ position, the linear actuator 180 stops outputting power, and the reset member 170 starts to work until resetting the driving end 151 to the $E_3$ position, which makes the driving member 150 complete the first reciprocating. The rotation amplitude of the driving member 150 is $S_1$-$S_2$ and $S_2$-$S_3$. During the first reciprocating rotation, the front end of the driving end pushes one tooth forward by a distance $h_1$, the drug infusion volume is $V_1$, and its reset distance is $h_3$. At this time, the infusion volume $V_1$ is regarded as the infusion increment in this first mode. When the next driving is performed, the linear actuator 180 outputs force again. During the advancing distance $h_3$, the driving end 151 just slides on the surface of the wheel teeth 141, and the driving wheel 140 does not rotate, nor does the drug infusion of the infusion system implement. When the front end of the driving end reaches the $E_2$ position and continues to advance by a distance of $h_4$, the front end of the driving end pushes the wheel teeth 141 to the $E_4$ position, so the driving wheel 140 rotates, implementing the drug infusion. When the linear actuator 180 stops outputting the force, the reset member 170 resets the driving end 151 to a certain position, such as the $E_5$ position, therefore, the driving member 150 completes the second reciprocating rotation, and the driving member 150 rotates by $S_3$-$S_4$ and $S_4$-$S_5$. During the second reciprocating rotation, the forward distance of the front end of the driving end is $(h_3+h_4)$, and the drug infusion volume is $V_2$. At this time, the infusion volume $V_2$ is the infusion increment in this second mode. Obviously, the driving member 150 only drives the driving wheel 140 to rotate under the rotation amplitudes $S_1$-$S_2$ and $S_2$-$S_4$ in these two modes. For the rotation amplitude $S_1$-$S_2$ is greater than the rotation amplitude $S_2$-$S_4$ (or $h_1>h_4$), $V_1>V_2$. Therefore, the infusion system of the embodiment of the present invention has two different infusion increments.

By analogy, the distance between $E_1$, $E_2$, $E_3$, $E_4$, $E_5$ can be arbitrarily selected, such as $h_1=h_2$, $h_{1=2}\ h_2$, $h_1=4\ h_2$, etc., the infusion system has a variety of different infusion increments. Or the force point S can also reach to the $S_6$ position, and $S_4$ and $S_6$ may not be the limit positions for the rotating of the driving member 150, which is not specifically limited herein.

It should be noted that, as described above, in the embodiment of the present invention, the infusion system does not necessarily implement drug infusion when the driving end 151 advances. Only when the driving end 151 pushes the wheel teeth 141 forward, the infusion system does.

Each rotation amplitude of the driving member 150 corresponds with an infusion increment. Therefore, a variety of different rotation amplitudes of the driving member 150 make the drug infusion system have a variety of different infusion increments. Taking insulin as an example, the infusion increment range of the drug infusion system in the embodiment of the present invention is 0.0005 U~0.25 U (here, the infusion increment range includes endpoint values, that is, the infusion increment includes 0.0005 U and 0.25 U). In some embodiments of the present invention, the infusion increment of the drug infusion system may includes 0.001 U, 0.0025 U, 0.005 U, 0.0075 U, 0.01 U, 0.025 U, 0.05 U, 0.075 U, 0.1 U, etc. Specifically, in the embodiment of the present invention, the infusion increment of the drug infusion system includes 0.005 U, 0.0075 U, 0.01 U, 0.025 U, and 0.05 U.

It should be noted that in the embodiment of the present invention, the insulin concentration is 100 U/ml. In other embodiments, the insulin concentration may also be 200 U/ml, 400 U/ml, etc., which is not specifically limited here.

It should be noted here that when $h_1=h_2$, the infusion increment of the infusion system always maintains $V_1$ with the rotation amplitude always maintaining $S_1$-$S_2$ and $S_2$-$S_1$, which makes the infusion relatively stable.

Another embodiment of the present invention can also increase the frequency of the force output by the linear actuator 180 or by the reset unit 170 to increase the frequency or the rate of the reciprocating rotation of the driving member 150, thereby increasing the infusion rate of the infusion system.

In addition, the infusion systems of other embodiments of the present invention can change the driving power output frequency of the linear actuator 180 or the reset unit 170, which makes infusion system have multiple infusion rates. Here, the change of the driving power output frequency of the linear actuator 180 or the reset unit 170 can change the rate of any single movement, the rate of the reciprocating movement, or the frequency of the reciprocating movement of the driving member 150.

Figure 8A:
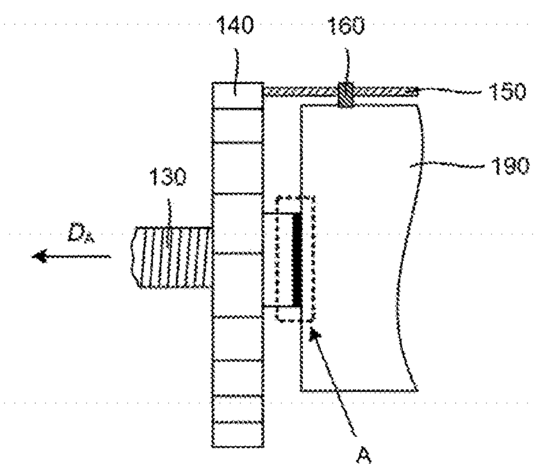
FIG. 8*a* and FIG. 8*b* are schematic diagrams of the driving wheel and the base, or the position limited member according to an embodiment of the present invention.
Figure 8B:
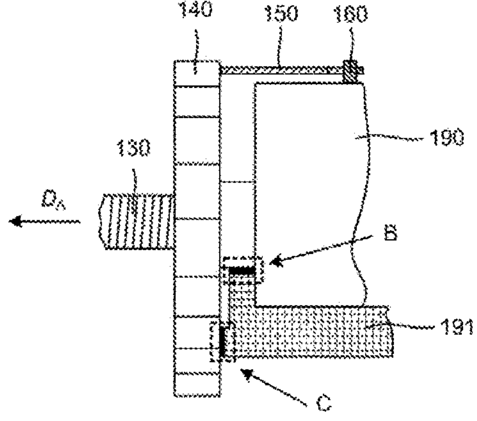

FIG. 8*a* and FIG. 8*b* are schematic diagrams of the driving wheel 140 and the base 190, or the position limited member 191 according to an embodiment of the present invention. FIG. 8*a* and FIG. 8*b* are front views of FIG. 4*c*.

When the driving end 151 slides on the surface of the wheel teeth 141, the driving end 151, contact with the wheel teeth 141, applies a certain pressure to the driving wheel 140 to ensure the non-rotating of the driving wheel 140. However, it is obvious that due to the structural features of the wheel teeth 141 and the circumference of the driving wheel 140, the pressure applied by the driving end 151 is not equal at different positions. Therefore, when the driving end 151 slides (including reset movement or sliding forward) on the surface of the wheel teeth 141, the driving wheel 140 may rotate forward or reverse, which affects the accuracy of the drug infusion volume and brings safety risk.

As shown in FIG. 8*a*, the driving wheel 140 is movably assembled on the base 190 remaining in frictional engagement. Here, the friction fit between these two means a certain friction force preset between two mutually moving structures, so as to the meaning of the following friction fit. In the embodiment of the present invention, the frictional force of the relative movement between the driving wheel 140 and the base 190 is applied or increased at the position A, indicated by the dotted frame, to ensure that when the driving end 151 slides on the surface of the wheel teeth 141, the driving wheel 140 stops rotating.

As shown in FIG. 8*b*, in another embodiment of the present invention, the infusion system further includes a position limited member 191 that is movably assembled on the base 190 to limit the position of the driving wheel 140. The position limited member 191 is in friction fit with the driving wheel 140 at position B or position C, indicated by the dotted frame. Similarly, in the embodiment of the present invention, the position limited member 191 increases the frictional force that the driving wheel 140 receives when rotating, also ensuring that the driving wheel 140 stops rotating when the driving end 151 slides on the surface of the wheel teeth 141. At the same time, the position limited member 191 can make full use of the internal space of the infusion system, and frictionally cooperate with the driving wheel 140 at multiple positions.

Other embodiments of the present invention do not limit the position of the above friction fit, as long as the condition for applying or increasing the friction force received by the second driving unit during movement is satisfied. For example, the friction force can also be applied on both sides of the driving wheel 140 at the same time. The embodiment of the present invention neither limits the material of the position limited member 191. For example, the position limited member 191 is an elastic member, a plastic member or a metal member.

Other embodiments of the present invention may increase the pressure of the driving end 151 on the wheel teeth 141 instead of providing the above-mentioned friction fit, which can increase the maximum static friction of the driving wheel 140 and also ensure the non-rotating of the driving wheel 140 when the driving end 151 slides on the surface of the wheel teeth 141.

Figure 9:
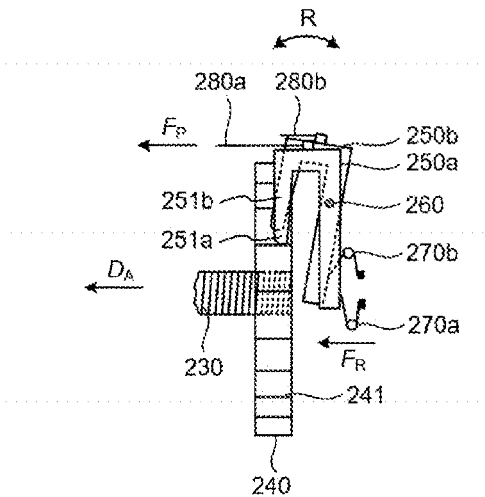
FIG. 9 is a schematic diagram of a driving unit including two driving members according to an embodiment of the present invention.
Figure 10:
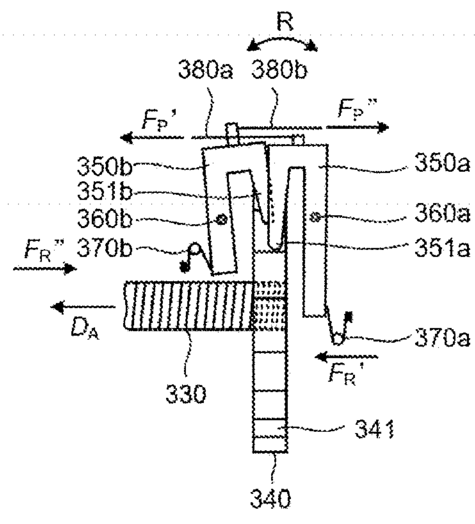
FIG. 10 is a schematic diagram of a driving unit including two driving members according to another embodiment of the present invention.

FIG. 9 and FIG. 10 are schematic diagrams of a driving unit including two driving members according to different embodiments of the present invention.

As shown in FIG. 9, the driving member 250*a* rotates reciprocally in the R direction around the rotating shaft 260 under the action of the linear actuator 280*a* and the reset unit 270*a*. Similarly, the driving member 250*b* rotates reciprocally in the R direction around the rotating shaft 260 under the action of the linear actuator 280*b* and the reset unit 270*b*. In the embodiment of the present invention, the reciprocating rotations of the two driving members do not interfere with each other. Therefore, both the driving member 250*a* and the driving member 250*b* can independently implement the driving method or principle described above.

Preferably, in the embodiment of the present invention, the driving member 250*a* and the driving member 250*b* rotate asynchronously. That is, when the driving end 251*a* of the driving member 250*a* pushes the wheel teeth 241 to move, the driving end 251*b* of the driving member 250*b* slides on the surface of the wheel teeth 241.

When the driving end 251*b* slides to one position, the control unit controls the linear actuator 280*a* to stop outputting driving power to the driving member 250*a*, and in turn controls the linear actuator 280*b* to output power to the driving member 250*b*. At this time, the driving member 250*a* rotates in the clockwise direction under the action of the reset unit 270*a*, and the driving end 251*a* slides on the surface of the wheel teeth, while the driving end 251*b* pushes the wheel teeth 241. The driving members 250*a* and 250*b* are alternately powered to push the driving wheels 240.

In the embodiment of the present invention, the pulling force $F_P$ of the linear actuators 280*a* and 280*b*, the elastic force $F_R$ of the reset units 270*a* and 270*b* and the forward direction $D_A$ of the screw 230 are shown in the figures. Like foregoing statement, the direction of the pulling force $F_P$ is parallel to the forward direction $D_A$ of the screw 230.

In the embodiment of the present invention, the types of the reset units 270*a* and 270*b* can be referred to the above, which will not be repeated herein.

As shown in FIG. 10, the driving ends 351*a* and 351*b* alternately push the wheel teeth 341, respectively, and the power output by the linear actuators 380*a* and 380*b* are both controlled by the control unit 101.

It should be noted that, in the embodiment of the present invention, the direction of the pulling force $F_P'$ of the linear actuator 380*a* and that of the pulling force $F_P''$ of the linear actuator 380*b* are opposite. Obviously, the direction of the resetting force $F_R'$ of the reset unit 370*a* and that of the resetting force $F_R''$ of the reset unit 370*b* are also opposite.

Also, in the embodiment of the present invention, the driving members 350*a* and 350*b* rotate asynchronously. That is, when the driving end 351*a* of the driving member 350*a* pushes the wheel teeth 341 to forward, the driving end 351*b* of the driving member 350*b* slides on the surface of the wheel teeth 341. When the driving end 351*b* slides to one position, the control unit controls the linear actuator 380*a* to stop outputting power to the driving member 350*a*, and in turn controls the linear actuator 380*b* to output power to the driving member 350*b*. The driving member 350*a* resets to the clockwise rotation by the reset unit 370*a*, while the driving end 351*a* slides on the surface of the wheel teeth 341, and the driving end 351*b* pushes the wheel teeth 341. The driving members 350*a* and 350*b* alternately pushes the driving wheels 340.

Similarly, both the driving member 350*a* and the driving member 350*b* can independently implement the driving method or principle described above. And the types of the reset units 370*a* and 370*b* can be referred to the above, which will not be repeated herein.

It should be noted that, in other embodiments of the present invention, more driving members can be arranged in the driving unit, or more driving ends are disposed on each driving member, or more driving wheels can also be provided in the infusion system. Therefore, different driving members respectively push the corresponding driving wheels to rotate.

Figure 11A:
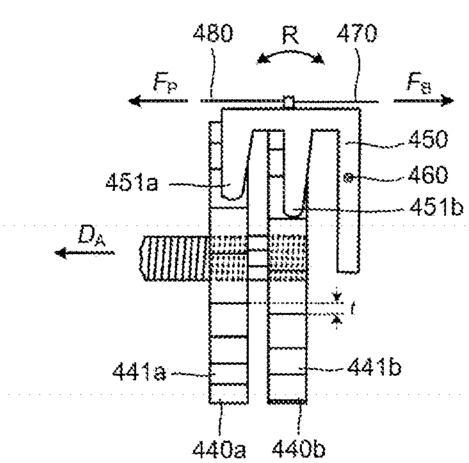
FIG. 11*a* and FIG. 11*b* are schematic diagrams of two driving ends of a driving member cooperating with two driving wheels, respectively according to yet another embodiment of the present invention.
Figure 11B:
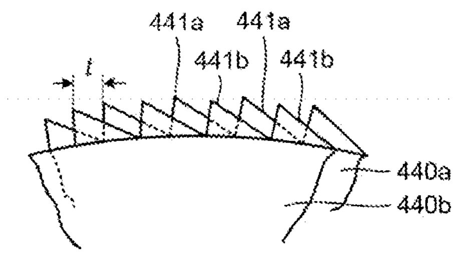

FIG. 11*a* and FIG. 11*b* are schematic diagrams of two driving ends 451*a* and 451*b* of a driving member 450 cooperating with two driving wheels 440*a* and 440*b* respectively according to yet another embodiment of the present invention. FIG. 11*b* is a right view of the partial teeth structure of the driving wheels 440*a* and 440*b* in FIG. 11*a*.

As shown in FIG. 11*a* and FIG. 11*b*, in the embodiment of the present invention, the driving member 450 includes two driving ends 451*a* and 451*b* disposed left and right, while two fixedly connected driving wheels 440*a* and 440*b* also disposed on the left and right (that is, two driving wheels can move simultaneously). The driving ends 451*a* and 451*b* cooperate with the driving wheels 440*a* and 440*b*, respectively, and the rotating shaft 460 is disposed on the same side of two driving wheels 440*a* and 440*b*. Both the linear actuator 480 and the reset unit 470 of the embodiment of the present invention are shape memory alloys, and the driving end 451*a* or 451*b* can respectively push the wheel teeth 441*a* or 441*b* forward. Their working principles and operating modes are consistent with the foregoing embodiments.

In addition to driving end 451*a* or 451*b* operating independently, the embodiment of the present invention can also adjust the distance between the front ends of the driving ends 451*a* and 451*b*, or adjust the offset degree of the wheel teeth 441*a* and 441*b* to make two driving ends 451*a* and 451*b* cooperate with each other. Preferably, in the embodiment of the present invention, the wheel teeth 441*a* and 441*b* are offset with degree t, as shown in FIG. 11*a* and FIG. 11*b*. The following teeth offset of two driving wheels have the same meaning here.

Obviously, in the embodiment of the present invention, two driving ends 451*a* and 451*b* reciprocate synchronously. As shown in FIG. 11*a*, when the previous forward movement is completed, the driving member 450 starts a reset movement, the driving end 451*a* reaches the driving position before the driving end 451*b*, so the driving end 451*a* can be used to start the next forward movement instead. Or the driving member 450 continues the reset movement until the driving end 451*b* reaches the next driving position to start the next forward movement. Of course, the driving member 450 may continue to be reset for a much larger distance, as described above. Here, the driving position refers to the position where the driving end can push the wheel teeth forward, as shown in the positions $E_1$ and $E_2$ in FIG. 7, and the following driving position has the same meaning as here.

Therefore, by controlling the rotation amplitude of the driving member 450, the driving end 451*a* or 451*b* can individually push the corresponding wheel teeth 441*a* or 441*b* forward, or the driving end 451*a* or 451*b* alternately pushes the wheel teeth forward, making the infusion system have multiple infusion increments.

Figure 12A:
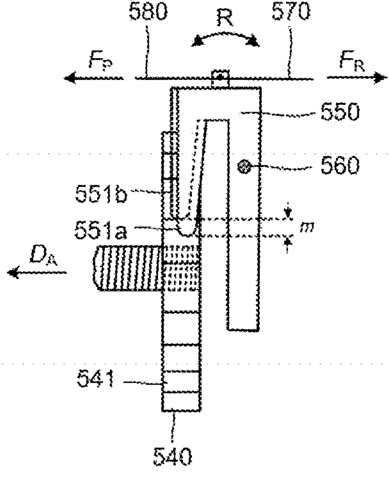
FIG. 12*a* and FIG. 12*b* are schematic diagrams of the driving member includes two driving ends disposed up and down according to yet another embodiment of the present invention.
Figure 12B:
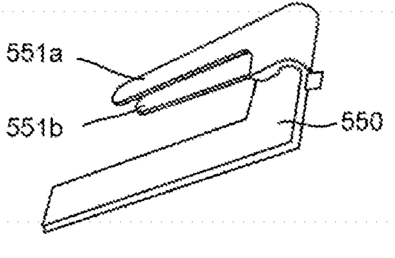

FIG. 12*a* and FIG. 12*b* are still another embodiment of the present invention in which the driving member 550 includes two driving ends 551*a* and 551*b* disposed up and down, and driving ends 551*a* and 551*b* cooperate with the same driving wheel 540. FIG. 12*b* is a perspective diagram of the driving member 550 in FIG. 12*a*.

As shown in FIG. 12*a* and FIG. 12*b*, the driving member 550 includes two driving ends 551*a* and 551*b* disposed up and down cooperating with the same driving wheel 540, so the driving ends 551*a* and 551*b* reciprocate synchronously. The front ends of the driving ends 551*a* and 551*b* are not level with a certain distance m, therefore, the two cannot simultaneously push the wheel teeth 541 forward, as shown in FIG. 12*a*. When the driving end 551*b* finishes the last forward movement, the driving member 550 performs a reset movement, obviously making the driving end 551*a* reach the next driving position before the driving end 551*b*. The driving end 551*a* can be used to push the wheel teeth 541 forward to start the next forward movement. Or the driving member 550 continues the reset movement until the driving end 551*b* reaches the next driving position to start the next forward movement. Of course, the driving ends 551*a* and 551*b* can also reset to a much larger distance, as described above.

Therefore, by controlling the power output by the linear actuator 580 or the reset unit 570, the driving member 550 has different rotation amplitudes, which makes the driving end 551*a* or 551*b* individually push the wheel teeth 541 forward or the two alternately push the wheel teeth 541 forward, thereby making the infusion system have a variety of different infusion increments.

In other embodiments of the present invention, the driving member may further include more driving ends, such as 3, 4 or more, which is not specifically limited herein.

When the drug infusion system has multiple infusion modes, the user, according to the actual requirements, can flexibly select the infusion mode to stabilize the level of body fluid parameters. Taking insulin stabilizing blood glucose levels as an example, some users or body tissues at the infusion site absorb insulin slowly. Users can choose an infusion mode with smaller infusion increment or lower infusion rate, which not only stabilizes the blood glucose level, but also improves the utilization of insulin, reducing the burden on body tissues. As another example, blood glucose spikes after a meal, so the user can first select an infusion mode with a relatively large infusion increment or a relatively high infusion rate to suppress the rapid rise in blood glucose, and then select an infusion mode with a medium infusion increment or infusion rate, and finally, choose an infusion mode with a relatively small infusion increment or a relatively low infusion rate to slowly stabilize blood glucose at a reasonable level. For another example, the bolus insulin required after each meal is different, and the body's basal insulin requirement is also different at different periods of one day. Therefore, multiple infusion modes of the infusion system can be flexibly selected (by the user or automatically by the closed-loop system) according to the actual requirements to achieve the goal of precise control of blood glucose levels.

In summary, in the unilaterally driven drug infusion system disclosed in the present invention, the sensing unit operatively connected to the control unit and used to sense or recognize the user's body movements, and different body movements represent different functional instructions, and according to the body movement sensed or recognized by the sensing unit, the control unit controls the infusion unit to execute corresponding functional instructions. Compared with manual inputting, body movements are directly used as functional instructions, avoiding the user from searching the inputting position of the functional instructions on the remote device and manual inputting, which is simple and convenient, and improves the user experience as well.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. A unilaterally driven drug infusion system, comprising:

an infusion unit, comprising:

a reservoir, a piston and a screw, wherein the piston, connected with the screw, is arranged in the reservoir;

a driving unit including at least one rotating shaft and at least one driving member, wherein the at least one driving member includes at least one driving end, and the driving member rotates around the rotating shaft to advance or reset the driving end;

at least one driving wheel provided with wheel teeth, wherein the driving end which is advancing pushes the wheel teeth to rotate the driving wheel, thereby driving the screw forward;

a linear actuator and a reset unit respectively connected to the driving member, wherein the linear actuator and the reset unit apply driving power to the driving member to advance and reset the driving end, respectively;

a control unit, wherein the control unit is connected to the linear actuator or the reset unit, controls the linear actuator or the reset unit to apply different driving powers on the driving member; and a sensing unit operatively connected to the control unit and used to sense or recognize body movements, wherein the body movements which are different represent different functional instructions, and according to the body movement sensed or recognized by the sensing unit, the control unit controls the infusion unit to execute a corresponding functional instruction of the functional instructions, wherein the rotating shaft and the reset unit are disposed on a base, a position of the driving end is fixed relative to the driving member, and the linear actuator deforms and shrinks to provide the driving power to the driving member after the linear actuator is energized.

2. A unilaterally driven drug infusion system of claim 1, wherein, the functional instructions include infusing drug or stopping infusing drug, priming an infusion needle, puncturing or retracting the infusion needle, adjusting an infusion speed or infusion mode, adjusting an amount of drug infusion, turning on or off an alarm, connecting or disconnecting a remote device, switching a physical state, or starting an event.

3. A unilaterally driven drug infusion system of claim 1, wherein, the sensing unit is provided with one or more of an acceleration sensor, an inclination sensor, a vibration sensor and a rotation sensor.

4. A unilaterally driven drug infusion system of claim 1, wherein, the body movements include one or a combination of jumping, squatting, leg movements, arm movements, taps on the sensing unit, bending over, torso twist, special way of walking.

5. A unilaterally driven drug infusion system of claim 4, wherein, the body movement sensed or recognized by the sensing unit within a fixed time period t is recognized as a valid body movement, and beyond the fixed time period t, the body movement is recognized as an invalid body movement.

6. A unilaterally driven drug infusion system of claim 5, wherein, the fixed time period t is 0.5 s-5 s.

7. A unilaterally driven drug infusion system of claim 6, wherein, the fixed time period t is 1 s.

8. A unilaterally driven drug infusion system of claim 1, wherein, the sensing unit is integrated in the infusion unit or the control unit.

9. A unilaterally driven drug infusion system of claim 8, wherein, the infusion unit and the control unit are designed separately, and a control mechanism module is reusable.

10. A unilaterally driven drug infusion system of claim 8, wherein, the infusion unit and the control unit are disposed in one housing, discarded together after a single use.

11. A unilaterally driven drug infusion system of claim 1, wherein, the sensing unit, the control unit and the infusion unit are arranged in one device.

12. A unilaterally driven drug infusion system of claim 11, wherein, the infusion unit and the control unit are designed separately, and a control mechanism module is reusable.

13. A unilaterally driven drug infusion system of claim 11, wherein, the infusion unit and the control unit are disposed in one housing, discarded together after a single use.

14. A unilaterally driven drug infusion system of claim 1, further comprising a body movement verification unit which is connected to the sensing unit.

15. A unilaterally driven drug infusion system of claim 1, wherein, the driving member has a variety of different operating modes, thereby making the unilaterally driven drug infusion system have various different infusion increments or infusion rates.

* * * * *